United States Patent
Ekre et al.

(10) Patent No.: US 9,475,888 B2
(45) Date of Patent: Oct. 25, 2016

(54) NON ANTI-COAGULATIVE GLYCOSAMINOGLYCANS COMPRISING REPEATING DISACCHARIDE UNIT AND THEIR MEDICAL USE

(71) Applicant: DILAFOR AB, Solna (SE)

(72) Inventors: Hans-Peter Ekre, Stockholm (SE); Ulf Lindahl, Uppsala (SE); Erik Holmer, Stockholm (SE); Per-Olov Eriksson, Strängnäs (SE)

(73) Assignee: Dilafor AB, Solna (SE)

( * ) Notice: Subject to any disclaimer, the term of this patent is extended or adjusted under 35 U.S.C. 154(b) by 128 days.

(21) Appl. No.: 14/366,624

(22) PCT Filed: Dec. 19, 2012

(86) PCT No.: PCT/SE2012/051433
§ 371 (c)(1),
(2) Date: Jun. 18, 2014

(87) PCT Pub. No.: WO2013/095279
PCT Pub. Date: Jun. 27, 2013

(65) Prior Publication Data
US 2015/0011505 A1 Jan. 8, 2015

Related U.S. Application Data

(60) Provisional application No. 61/577,223, filed on Dec. 19, 2011.

(51) Int. Cl.
| | | |
|---|---|---|
| C08B 37/00 | (2006.01) | |
| A61K 31/727 | (2006.01) | |
| A61K 9/00 | (2006.01) | |
| A61K 9/08 | (2006.01) | |

(52) U.S. Cl.
CPC ......... *C08B 37/0075* (2013.01); *A61K 9/0019* (2013.01); *A61K 9/08* (2013.01); *A61K 31/727* (2013.01)

(58) Field of Classification Search
CPC .... A61K 9/08; A61K 9/0019; A61K 31/727; C08B 37/0075
USPC .............................................. 514/56; 536/21
See application file for complete search history.

(56) References Cited

U.S. PATENT DOCUMENTS

| | | | |
|---|---|---|---|
| 4,303,651 A | 12/1981 | Lindahl et al. | |
| 4,990,502 A | 2/1991 | Lormeau et al. | |
| 5,250,519 A | 10/1993 | Conrad et al. | |
| 5,280,016 A | 1/1994 | Conrad et al. | |
| 5,472,953 A | 12/1995 | Ekre et al. | |
| 5,527,785 A | 6/1996 | Bevilacqua et al. | |
| 5,767,269 A * | 6/1998 | Hirsh | C08B 37/0078 514/56 |
| 5,993,810 A | 11/1999 | Lebovitz | |
| 6,028,061 A | 2/2000 | Bernfield et al. | |
| 6,486,137 B1 | 11/2002 | Lundqvist et al. | |
| 6,569,840 B1 * | 5/2003 | Yamashina | C08B 37/0075 514/56 |
| 6,596,705 B1 | 7/2003 | Varki et al. | |
| 8,071,569 B2 | 12/2011 | Mousa | |
| 2005/0075314 A1 | 4/2005 | Ekman-Ordeberg et al. | |
| 2005/0215519 A1 | 9/2005 | Viskov et al. | |
| 2006/0040896 A1 * | 2/2006 | Kennedy | A61K 31/727 514/56 |
| 2006/0147415 A1 | 7/2006 | Mousa et al. | |
| 2007/0021378 A1 * | 1/2007 | Varki | A61K 31/727 514/56 |
| 2010/0298263 A1 | 11/2010 | Casu et al. | |
| 2010/0316640 A1 | 12/2010 | Sundaram et al. | |
| 2010/0324276 A1 * | 12/2010 | Sundaram | A61K 31/727 536/21 |
| 2011/0200673 A1 | 8/2011 | Mousa | |

FOREIGN PATENT DOCUMENTS

| | | | | |
|---|---|---|---|---|
| EP | 0735050 A2 * | 10/1996 | ............. | C08B 37/10 |
| EP | 0867452 A1 | 9/1998 | | |
| EP | 1059304 A1 | 12/2000 | | |
| EP | 0735050 B1 | 9/2002 | | |
| EP | 0735050 B1 * | 10/2002 | ............. | C08B 37/00 |
| UA | 21707 | 3/2007 | | |
| WO | 92/02232 A1 | 2/1992 | | |
| WO | WO9408595 A1 | 4/1994 | | |
| WO | 03/055499 A1 | 7/2003 | | |
| WO | 03/088980 A1 | 10/2003 | | |
| WO | 2007/014155 A2 | 2/2007 | | |
| WO | 2009007224 A1 | 1/2009 | | |
| WO | 2009/059284 A2 | 5/2009 | | |
| WO | 2009/073184 A1 | 6/2009 | | |
| WO | 2009/124266 A2 | 10/2009 | | |
| WO | 2010/121196 A1 | 10/2010 | | |
| WO | 2011/000032 A1 | 1/2011 | | |
| WO | 2013/095276 A1 | 6/2013 | | |
| WO | 2013/095277 A1 | 6/2013 | | |

(Continued)

OTHER PUBLICATIONS

Lau et al, Clinical and Experimental Pharmacology and Physiology, 2010, 37(4), 417-421.*

(Continued)

*Primary Examiner* — Ganapathy Krishnan
(74) *Attorney, Agent, or Firm* — LeClairRyan, a Professional Corporation

(57) ABSTRACT

The present invention relates to a chemically modified glycosaminoglycan with an antifactor II activity of less than 10 IU/mg, an antifactor Xa activity of less than 10 IU/mg and an average molecular weight (Mw, weight average) from about 4.6 to 6.9 kDa. Also disclosed is a method of preparing the modified glycosaminoglycan and its medical uses.

24 Claims, 1 Drawing Sheet

(56) References Cited

FOREIGN PATENT DOCUMENTS

| WO | 2013/147689 A1 | 10/2013 |
|---|---|---|
| WO | 2013/147690 A1 | 10/2013 |

OTHER PUBLICATIONS

Ekman-Ordeberg et al., "Tafoxiparin a New Drug Counteracting Labor Arrest by Increased Myometiral Contractility and Enhanced Cervical Cytokine Synthesis," Poster Presentation at Birth Labor Congress (Chicago, 2011) and Society of Gynecologic Investigations (Miami, 2010).
Dilafor press release: Promising Results from Phase II Trial Show New Treatment from Dilafor Prevents Protracted Labor in Childbirth (Sep. 3, 2009).
Barragan et al., "The Duffy-Binding-Like Domain 1 of Plasmodium falciparum Erythrocyte membrane Protein 1 (PfEMP1) is a Heparan Sulfate Ligand that Requires 12 Mers for Binding," Blood 95(11):3594-3599 (2000).
Skidmore et al., "Disruption of Rosetting in Plasmodium falciparum Malaria with Chemically Modified Heparin and Low Molecular Weight Derivatives Possessing Reduced Anticoagulant and Other Serine Protease Inhibition Activities," J. Med. Chem. 51:1453-1458 (2008).
Wiesner et al., "New Antimalarial Drugs," Angew. Chem. Int. Ed. 42:5274-5293 (2003).
Ekman-Ordeberg et al., "Does Low Molecular Weight Heparin Shorten Term Labor?" Acta Obstreticia et Gynecologica Scandinavica 89(1):147-150 (2010).
Lau et al., "Inhibitors of Slit Protein Interactions with the Heparan sulphate Proteoglycan Glypican-1: Potential Agents for the Treatment of Spinal Cord Injury," Clinical and Experimental Pharmacology and Physiology 37(4):417-421 (2010).
International Search Report and Written Opinion for PCT/SE2012/051433 (mailed Mar. 28, 2013).
Bazin et al., "Inhibition of Apolipoprotein E-Related Neurotoxicity by Glycosaminoglycans and their Oligosaccharides," Biochem. 41:8203-8211 (2002).
Garg et al., "Heparin Oligosaccharide Sequence and Size Essential for Inhibition of Pulmonary Artery Smooth Muscle Cell Proliferation," Carb. Res. 337:2359-2364 (2002).
Guerrini et al., "Antithrombin-Binding Octasaccharides and Role of Extensions of the Active Pentasaccharide Sequence in the Specificity and Strength of Interaction. Evidence for Very High Affinity Induced by an Unusual Glucuronic Acid Residue," J. Biol. Chem. 283(39):26662-26675 (2008).
Leitgeb et al., "Low Anticoagulant Heparin Disrupts *Plasmodium falciparum* Rosettes in Fresh Clinical Isolates," Am. J. Trop. Med. Hyg. 84(3):390-396 (2011).
Suda et al., "Structural Characterization of Heparin's Binding Domain for Human Platelets," Thromb. Res. 69:501-508 (1993).
Vogt et al., "Release of Sequestered Malaria Parasites Upon Injection of a Glycosaminoglycan," PLOS Path. 2 (9):0853-0863 (2006).
Dondorp et al., "Levamisole Inhibits Sequestration of Infected Red Blood Cells in Patients with Falciparum Malaria," J. Infect. Dis. 196:460-466 (2007).
Silamut et al., "A Quantitative Analysis of the Microvascular Sequestration of Malaria Parasites in the Human Brain," Am. J. Pathol. 155(2):395-410 (1999).
Dilafor press release: Potential Treatment for Severe Malaria completes Phase I Study (Oct. 13, 2009).
Dilafor press release: Dilafor Announces the Selected INN for DF02, Sevuparin (Aug. 30, 2010).
Dilafor press release: Dilaforette Initiates a Phase I/II Study with Sevuparin for the Treatment of Severe Malaria (Sep. 23, 2011).
WHO Drug Information, 25(4):437-438 (2011).
WHO Drug Information, 26(3):323 (2012).
Lindahl et al., "Evidence for a 3-O-Sulfated D-Glucosamine Residue in the Antithrombin-Binding Sequence of Heparin," Proc. Nat. Acad. Sci. U.S.A. 77(11):6551-6555 (1980).
Casu et al., "Undersulfated and Glycol-Split Heparins Endowed with Antiangiogenic Activity," J. Med. Chem. 47:838-848 (2004).
Naggi et al., "Glycol-Splitting as a Device for Modulating Inhibition of Growth Factors and Heparanase by Heparin and Heparin Derivatives," Chemistry and Biology of Heparin and Heparin Sulfate, Elsevier, Amsterdam pp. 461-476 (2005).
Naggi et al., "Modulation of the Heparanase-Inhibiting Activity of Heparin through Selective Desulfation, Graded N-Acetylation, and Glycol Splitting," J. Biol. Chem. 280(13):12103-12113 (2005).
Pisano et al., "Undersulfated, Low-Molecular-Weight Glycol-Split Heparin as an Antiangiogenic VEGF Antagonist," Glycobiol. 15(2):1C-6C (2005).
Alekseeva et al., "Profiling Glycol-Split Heparins by HPLC/MS Analysis of their Heparinase-Generated Oligosaccharides," Anal. Biochem. 434(1):112-122 (2013).
Alekseeva et al., "Structural Features of Glycol-Split Low-Molecular-Weight Heparins and their Heparin Lyase Generated Fragments," Anal. Bioanal. Chem. 406:249-265 (2014).
Clinicaltrials.gov: A Phase I/II, Randomized, Open Label, Active Control, Parallel Assignment, Safety/Efficacy Study of Sevuparin/DF02 as an Adjunctive Therapy in Subjects Affected with Uncomplicated Falciparum Malaria (May 7, 2015).
Carlson et al., "Disruption of Plasmodium Falciparum Erythrocyte Rosettes by Standard heparin and Heparin Devoid of Anticoagulant Activity," Am. J. Trop. Med. Hyg. 46(5):595-602 (1992).
von der Lehr, "Battle Against Clever Parasite," Kemisk Tidskrift Nr 7-8:24-26 (2011).
Kulane et al., "Effect of Different Fractions of Heparin on Plasmodium Falciparum Merozoite Invasion of Red Blood Cells in Vitro," Am. J. Trop. Med. Hyg. 46(5):589-594 (1992).
Ware et al., "Advances in the Use of Hydroxyurea," Am. Soc. Hematol. pp. 62-65 (2009).
Chaplin et al., "Preliminary Trial of Minidose Heparin Prophylaxis for Painful Sickle Cell Crises," E. African Med. J. 66 (9):574-584 (1989).
Qari et al., "Reduction of Painful Vaso-Occlusive Crisis of Sickle Cell Anaemia by Tinzaparin in a Double-Blind Randomized Trial," Thromb. Heamost. 98:392-396 (2007).
Blumenkrantz et al., "New Method for Quantitative Determination of Uronic Acids," Analytical Biochem. 54:484-489 (1973).
Bachelet et al., "Affinity of Low Molecular Weight Fucoidan for P-Selectin Triggers its Binding to Activated human Platelets," Biochimica Biophysica Acta 1790:141-146 (2009).
Zennadi et al., "Epinephrine Acts Through Erythroid Signaling Pathways to Activate Sickle Cell Adhesion to Endothelium via LW-{alpha}v{beta}3 Interactions," Blood 104:3774-3781 (2004).
Zennadi et al., "Epinephrine-Induced Activation of LW-Mediated Sickle Cell Adhesion and Vaso-Occlusion In Vivo," Blood 110:2708-2717 (2007).
Batchvarova et al., "Sevuparin Reduces Adhesion of Both Sickle Red Cells and Leukocytes to Endothelial Cells In Vitro and Inhibits Vaso-Occlusion In Vivo," Abstract #58733, New Orleans 7-10 (Dec. 2013) (ASH).
Brodszki et al., "A Novel Treatment Approach for Paediatric Gorham-Stout Syndrome with Chylothorax," Acta Paediatrica 100:1448-1453 (2011).
Fransson et al., "Structural Studies on Heparan Sulphates. Characterization of Oligosaccharides; Obtained by Periodate Oxidation and Alkaline Elimination," Eur. J. Biochem. 106:59-69 (1980).
Guerrini et al., "Complex Glycosaminoglycans: Profiling Substitution Patterns by Two-Dimensional Nuclear Magnetic Resonance Spectroscopy," Analytical Biochem 337:35-47 (2005).
Shaker et al., "Uterine Contractions Due to Heparin," British Med. J. pp. 408-409 (1974).
Osmers et al., "Glycosaminoglycans in Cervical Connective Tissue During Pregnancy and Parturition," Obst. Gynecol. 81(1):88-92 (1993).
Blanks et al., "Myometrial Function in Prematurity," Best Pract. Res. Clin. Obst. Gynaecol. 21(5):807-819 (2007).

(56) References Cited

OTHER PUBLICATIONS

Fransson et al., "Relationship Between Anticoagulant Activity of Heparin and Susceptibility to Periodate Oxidation," FEBS Lett. 97(1):119-123 (1979).
Su, "Postpartum Hemorrhage," Prim. Care Clin. Office Pract. 39:167-187 (2012).
Belghiti et al., "Oxytocin During Labour and Risk of Severe Postpartum Haemorrhage: A Population-Based, CohortNested Case-Control Study," BMJ Open 1(e000514):1-9 (2011).
Ekman-Ordeberg et al., "Low Molecular Weight Heparin Stimulates Myometrial Contractility and Cervical Remodeling In Vitro," Acta Obstetricia et Gynecologica 88:984-989 (2009).
Hjelm Cluff et al., "Prolonged Labour Associated with Lower Expression of Syndecan 3 and Connexin 43 in Human Uterine Tissue," Reproduc. Biol. Endocrinol. 4:24 (2006).
Akerud, "Uterine Remodeling During Pregnancy. Studies on the Effect of Heparin/Heparan Sulfate," Department of Experimental Medical Science (2009).
International Nonproprietary Names for Pharmaceutical Substances: List 64, p. 24.
WHO Drug Information 23(4) Proposed International Nonproprietary Names for Pharmaceutical Substances: List 102 (2009).
Karolinska Development Press Release—Portfolio Company Completes Successful Phase II Clinical Trial (Sep. 4, 2009).
Invitation to Subscribe for Shares in Karolinska Development p. 45 (Mar. 25, 2011) p. 46 (Apr. 14, 2011).
Clinicaltrials.gov: A Randomized, Double-Blind, Placebo-Controlled, Multicenter Trial to Assess the Safety and Efficacy or Pre-Treatment With DF01 During Late Pregnancy in Reducing Prolonged Labor (May 19, 2015).
Roos et al., "Prostaglandin Receptors in the Human Cervix at Term and Post Term Pregnancy—Genetic Expression and Localization," Poster S-071 Reproduct. Sci. 18(4):Supplement (Mar. 2011).
Kadanali et al., "Comparison of Labor Induction with Misoprostol vs. Oxytocin/Prostaglandin E2 In Term Pregnancy," International Journal of Gynecology & Obstetrics 55:99-104 (1996).
Belayet et al., "Binding of Interleukin-8 to Heparan Sulphate Enhances Cervical Maturation in Rabbits," Molecular Human Reproduction 5(3):261-269 (1999).
Combs et al., "Factors Associated With Hemorrhage In Cesarean Deliveries," Obstetrics and Gynecology, 77:77-82 (1991).
Henry et al., "Perinatal Outcomes in the Setting of Active Phase Arrest of Labor," Obstetrics and Gynecology, 112(5): 1109-1115 (2008).
Isma et al., "The Effect of Low Molecular Weight Heparin (Dalteparin) on Duration and Initiation of Labour," J Thromb Thrombolysis 30:149-153 (2010).
The Merck Manual of Diagnosis and Therapy, 17th Ed., Beers and Berkow, Eds., Ch. 253. "Abnormalities And Complications of Labor and Delivery,"; Ch. 254: "Postpartum Care"; pp. 2062-2067 (1999).
Van Lennep et al., "Prophylaxis with Low-Dose Low-Molecular-Weight Heparin During Pregnancy and Postpartum: Is It Effective?," Journal of Thrombosis and Haemostasis, 9:473-480 (2011).
Yousuf and Haider, "Postpartum Hemorrhage: An Experience At Tertiary Care Hospital," Journal of Surgery Pakistan (International), 14(2):80-84 (2009).
Rudd et al., "High-Sensitivity Visualization of Contaminants in Heparin Samples by Spectral Filtering of $^1$H NMR Spectra," Analyst 136:1390-1398 (2011).
Wei et al., "High-Dose vs Low-Dose Oxytocin for Labor Augmentation: A Systematic Review," Am. J. Obstetrics & Gynecology 203(4): 296-304 (2010).
Office Action in U.S. Appl. No. 14/387,929, (mailed Apr. 7, 2016).
Alfirevic et al.,"Prevention of Post-Partum Hemorrhage with Misoprostol," Int. J. Gynecology Obstetrics 99:S198-S201 (2007).
Dildy, "Postpartum Hemorrhage: New Management Options," Clinc. Obstetrics & Gynecology 45(2):330-344 (2002).
Office Action in U.S. Appl. No. 14/399,450, (mailed Apr. 5, 2016).
Office Action in U.S. Appl. No. 14/387,936, (mailed Apr. 6, 2016).

\* cited by examiner

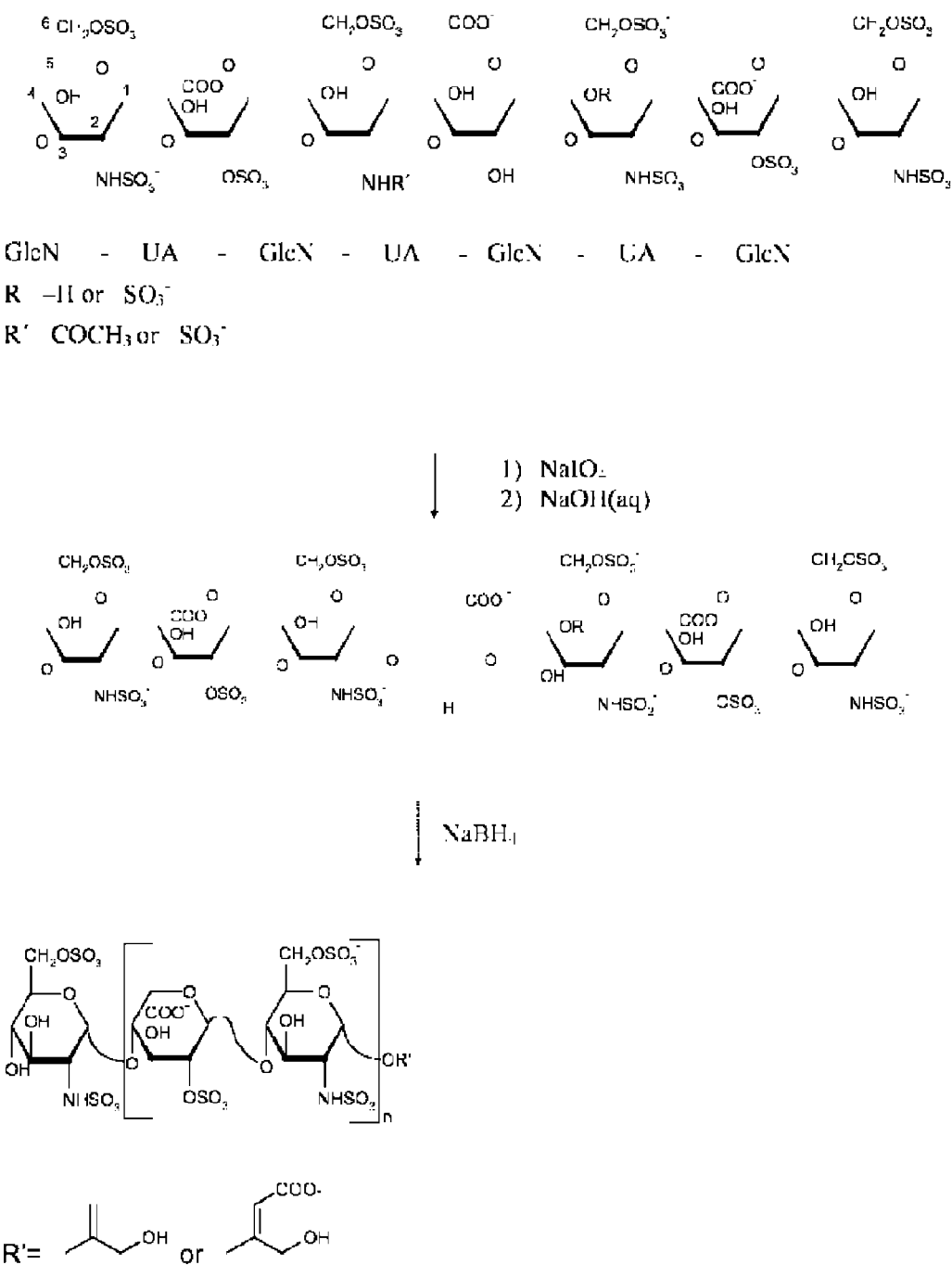

NON ANTI-COAGULATIVE GLYCOSAMINOGLYCANS COMPRISING REPEATING DISACCHARIDE UNIT AND THEIR MEDICAL USE

This application is a national stage application under 35 U.S.C. §371 of PCT Patent Application No. PCT/SE2012/051433, filed Dec. 19, 2012, which claims the priority benefit of U.S. Provisional Application Ser. No. 61/577,223, filed Dec. 19, 2011.

FIELD OF THE INVENTION

The present invention relates to new modified glycosaminoglycans with low anticoagulant activity and method of their production. The method of production is specifically adapted to produce modified heparins and heparin sulphates with high bioavailability following for example parenteral injection and high structural stability resulting in favourable storage and handling properties.

BACKGROUND

Heparin is a polydisperse, naturally occurring polysaccharide that inhibits coagulation, the process whereby thrombosis occurs. Heparin consists of unbranched polysaccharide chains of varying lengths and molecular weights. Chains of molecular weight from 5000 to over 40,000 daltons, make up pharmaceutical-grade heparin.

Heparin, derived from natural sources, mainly porcine intestine or bovine lung tissue, can be administered therapeutically for prevention and treatment of thrombosis. However, the effects of unfractionated heparin can be difficult to predict. During treatment of thrombosis with unfractionated heparin, coagulation parameters must be monitored very closely to prevent over- or under-anticoagulation.

Numerous brands of heparins and low molecular weight heparins (LMWH), such as dalteparin and enoxaparin are available for the treatments that rely on their anti-coagulant activity. A large number of in vitro and animal experimental investigations, and even clinical trials, indicate that heparin and its derivatives have beneficial properties others than those related to its anticoagulant effect. However, existing heparins and LMWH are not suitable for treating other medical conditions because of the bleeding risk associated with the anticoagulant effect. Although LMWHs represent significant clinical advantages compared to heparin, this class of substances, by definition, still retain high anticoagulant activity that can give rise to potentially life threatening side-effects.

Because it can be given subcutaneously and does not require APTT monitoring, LMWH permits outpatient treatment of conditions such as deep vein thrombosis or pulmonary embolism that previously mandated inpatient hospitalization for unfractionated heparin administration.

The LMWH dalteparin has been shown to decrease protracted labor in women receiving prophylaxis for deep venous thrombosis. The mechanism is believed to involve dalteparin-induced increased levels of interleukins resulting in a favourable inflammatory reaction that promotes ripening of the cervix. Further, dalteparin has been shown to increase contractility of the uterus (Acta Obstetricia et Gynecologica, 2010; 89:147-150).

However, heparin and LMWH are not suitable for preventing or treating such maladies for a number of reasons. First, heparin and LMWH have significant, well-known anti-coagulant effects that restrict their use in late pregnancy and during delivery, both for prophylactic and acute use, due to the bleeding risk. For example the use of dalteparin is strictly contraindicated when epidural anesthesia is given, a measure frequently taken during child birth. Second, heparin has been associated with heparin-induced thrombocytopenia, a severe immune-mediated drug reaction that can occur in any patient exposed by heparin. It is a potentially devastating prothrombotic disease caused by heparin-dependent antibodies that develop either after a patient has been on heparin for 5 or more days or if the patient has had previous heparin exposure. Another untoward possible effect of long term treatment with heparin is that it may induce demineralization of bones and cause osteoporosis.

There have been many attempts to eradicate or reduce the anticoagulant activity of heparins or low molecular weight heparins in order to provide low anticoagulant heparins (LANs) which aim to benefit from other potential clinical effects from the heparin chains than the anticoagulant effect, without carrying the risk of untoward effects associated with heparin, predominantly bleeding. However, there is limited clinical experience of this type of heparins and so far no such products are allowed for clinical use European Patent 1059304 discloses enzymatically degraded or oxidized heparin resulting in a product with low anticoagulant effect, having an average molecular weight of 9 to 13 kDa, which is suggested for the treatment of neurodegenerative diseases.

U.S. Pat. No. 4,990,502 demonstrates one way of treating native heparin to cleave residues of the pentasaccharide residues responsible for the anticoagulant effect and a following depolymerization that results in a low anticoagulant, low molecular weight heparin with a an average molecular weight 5.8 to 7.0 kDa. In U.S. Pat. No. 4,990,502 time consuming methods, such a dialysis for about 15 hours, are used to terminate the oxidation process. Such processes could affect the molecular weight distribution of the final product. Controlling the molecular weight and the length of the polysaccharide chains is crucial to obtain the desired biological effect of the compound.

The bioavailability of long chain heparins after subcutaneous dosing is low and the possibility of heparin induced thrombocytopenia (HIT) induction is also positively correlated to the chain lengths. To reduce these clinically undesired properties the heparin derivative should not be of full length. Heparin chains of certain molecular weight can be obtained by fractionation of standard heparin. However, the production of heparin derivatives of intermediate or low molecular weight by fractionation methods such as gelfiltration, alcohol precipitation and ion exchange chromatography is associated with a significant waste of raw material as high molecular mass heparins are thus discarded.

The present invention, as outlined in the following sections describes a new process wherein the polysaccharide chains are shortened and a suitable average molecular weight distribution will be achieved favoring its clinical use and reducing the risk associated with the largest polysaccharide chains together with a minimal loss of raw material.

SHORT DESCRIPTION OF THE FIGURE

FIG. 1 shows a scheme of the synthesis of a low anticoagulant heparin according to the invention.

SUMMARY

The present invention relates to chemically modified glycosaminoglycans selected from heparins and heparan sulfates with an antifactor IIa activity of less than 10 IU/mg, an antifactor Xa activity of less than 10 IU/mg and an average molecular weight (weight average, Mw) from about 4.6 to 6.9 kDa, wherein:

the polysaccharide chains have from 2 to 20 (n in Formula I) polymer disaccharide units corresponding to molecular weights between 1.2 and 12 kDa;

the predominantly occurring saccharide is (Formula I)

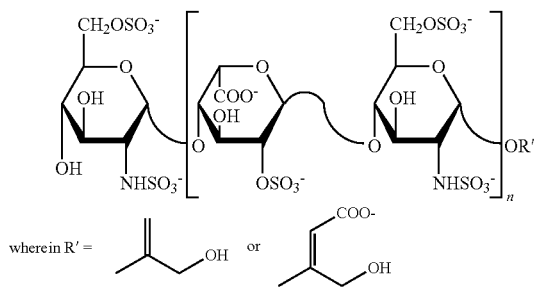

n is an integer from 2 to 20.

The invention further relates to uses thereof and method for its production.

DETAILED DESCRIPTION OF THE INVENTION

In general terms, the present invention relates to chemically modified heparins and heparan sulfates that are selectively prepared to retain therapeutic effects from the polysaccharide chains and to produce an optimal size distribution of the polysaccharide chains to ensure high bioavailability and stability while also having a low anticoagulant effect and thereby essentially eliminating the risk of bleeding.

The present invention will also ensure a high yield process which can be scaled up to produce a marketed product with a favorable cost of goods. Both the cost of production and the availability of raw materials become important factors in procuring a drug product. The possibility of modifying unfractionated heparins into a pharmacologically acceptable derivative with a favorable chain length distribution enables parenteral administration with a high bioavailability. Further this would enable off clinic treatment, such as self-treatment, which is beneficial from a socio-economic perspective.

A number of terms and definitions are used in the following context of describing the invention in a general and in a detailed or experimental context.

It must be noted that, as used in this specification and the appended claims, the singular forms "a," "an," and "the" include plural referents unless the context clearly dictates otherwise.

Also, the term "about" is used to indicate a deviation of +/−2% of the given value, preferably +/−5%, and most preferably +/−10% of the numeric values, where applicable.

Heparin is a naturally occurring glycosaminoglycan that is synthesized by and stored intracellulary in so-called mast cells in humans and animals. Prepared industrially, mostly from porcine intestinal mucosa, heparin is a potent anticoagulant and has been used clinically for more than 60 years as the drug of preference for prophylaxis and treatment of thromboembolic disorders. The major potential adverse effects of heparin treatment are bleeding complications caused by its anticoagulant properties.

Heparin is highly polydisperse and composed of a heterogeneous population of polysaccharides with molecular weights ranging from 5 to 40 kDa, with the average being approximately 15 to 18 kDa.

Low molecular weight/mass heparins (LMWH) according to European pharmacopeia are defined as "salts of sulfated GAGs having a mass-average molecular mass less than 8 kDa and for which at least 60 percent of the total mass has a molecular mass less than 8 kDa. They display different chemical structures at the reducing or the non-reducing end of the polysaccharide chains. The potency is not less than 70 IU of anti-factor Xa activity per milligram calculated with reference to the dried substance. The ratio of anti-factor Xa activity to anti-factor IIa activity is not less than 1.5." Clinically used LMWHs have molecular weights ranging from 3 to 15 kDa with an average of approximately 4 to 7 kDa. Produced by controlled depolymerization of heparin, LMWHs exhibits more favorable pharmacological and pharmacokinetic properties compared to unfractionated heparin, including a lower tendency to induce hemorrhage, increased bioavailability and a prolonged half-life following subcutaneous injection.

Heparan sulfate is a linear polysaccharide, overall less sulfated than heparin, which can be prepared from porcine intestinal mucosa or from bovine lung, from heparin side fractions using cetylpyridinium chloride fractionation and sequential salt extraction as described by Fransson et al., Structural studies on heparan sulfates, Eur. J. Biochem. 106, 59-69 (1980). Heparan sulfate is composed of alternating glucosamine and uronic acid residues, the resulting disaccharide units being either N-acetylated, N-sulfated or (to a minor extent) N-unsubstituted, and arranged mainly in domain-wise manner. Some heparan sulfates possess anticoagulant activity depending on the presence of a specific anticoagulant pentasaccharide, however considerably less than heparin.

Heparin exerts its anticoagulant activity primarily through high-affinity binding to and activation of the serine proteinase inhibitor, antithrombin (AT). AT, an important physiological inhibitor of blood coagulation, neutralizes activated coagulation factors by forming a stable complex with these factors. Binding of a specific pentasaccharide within the polysacharide chains of heparin causes a conformational change in AT that dramatically enhances the rate of inhibition of coagulation factors, thereby attenuating blood coagulation and the formation of blood clots.

The unique, specific pentasaccharide sequence, distributed randomly within heparin polymers, is essential for the binding to AT. Several structural characteristics of this sequence have been shown to be crucial for the interaction of heparin with AT. Notably, the iduronic acid residue present in this pentasaccharide sequence is consistently sulfated at the C-2 position; whereas the hydroxyl groups at both C-2 and C-3 of the glucuronic acid are unsubstituted (Formula II).

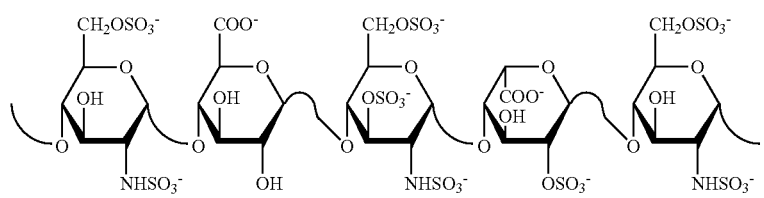

Formula II

Structural variants compatible with anticoagulant activity include N-acetyl rather than N-sulfate substitution of the GlcN unit toward the non-reducing terminal, and unsubstituted rather than 6-O-sulfated C6-hydroxyl groups at the other two GlcN residues.

By applying the herein disclosed process the interaction with AT is disabled and thus the anticoagulation activity is essentially depleted In the context of the present invention, anti-coagulant activity of the glycosaminoglycan relates to the clinical function of potentiating inhibition of coagulation factors Xa and IIa (thrombin) by AT. In one embodiment there is essentially no anticoagulant activity of the chemically modified glycosaminoglycans according to the invention.

In the process of preparing a low anticoagulant heparin it is important to avoid, or counteract non-specific depolymerization, i.e. depolymerization effects not attributable to the predictable results obtained from the hydrolysis from the alkaline beta-elimination, the depolymerization step per se. Non-specific depolymerization may result in unpredictable loss in molecular weight, discolored products (with unstable absorbance values), other stability issues and the appearance of unidentified residues and residues not predicted to arrive from processing of heparin or low molecular weight heparins. Products subjected to non-specific depolymerization may obtain unfavourable and unstable molecular weight distribution of the polysaccharides.

One important aspect of the invention is to control depolymerization in order to obtain a product with optimal chain distribution and favorable stability features. In one aspect the depolymerization is controlled by controlling the conditions under which periodate and also the resulting iodate are admitted to exert their oxidative attack on heparin. The method according to the invention has been optimized to minimize non-specific depolymerization that negatively affects the chain distribution and stability.

Other terms will be defined in relevant contexts in the following description.

In one aspect, the invention relates to a method of preparing chemically modified glycosaminoglycans selected from heparins and heparan sulfates with an antifactor IIa activity of less than 10 IU/mg, an antifactor Xa activity of less than 10 IU/mg and an average molecular weight (weight average, Mw) from about 4.6 to about 6.9 kDa. The method generally comprises a step of selectively oxidizing unfractionated heparin or heparan sulfate present in an aqueous solution by subjecting it to an oxidizing agent capable of oxidizing non-sulfated uronic acids and reducing the resulting oxidized saccharides. The method also generally comprises depolymerizing the heparin chains by basic hydrolysis.

In one aspect the method comprises the following steps:
oxidation of glucuronic and iduronic acids by treatment with periodate.

eliminating or minimizing the effects of oxidizing iodine-containing compounds,
depolymerization of polysaccharide chains under alkaline conditions (a beta elimination process), and
reduction and stabilizing of terminal aldehyde groups through a reaction with a reducing agent, such as $NaBH_4$.

In a further aspect the method also comprises one or more of the following steps:
final purification of the product by means of removing borate (oxidized $NaBH_4$), removal of small glycosaminoglycan fragments, addition of counter-ions and isolation of the product in a solid form.
drying of the product under vacuum and heat or as a lyophilization process to enable long term storage of product
dissolution and formulation of product in an aqueous phosphate buffered solution, adjustment of pH to 6-8. Addition of excipients for the purpose of tonicity adjustment,
aseptic filling of product into vials or syringes or lyophilization in the same In one aspect, the method is performed in the sequence of oxidizing, depolymerizing with hydrolysis and reducing and more specifically comprising the following steps:
a) oxidation of glucuronic and iduronic acids by treatment with periodate.
b) eliminating or minimizing the effects of oxidizing iodine-containing compounds,
c) depolymerization of polysaccharide chains under alkaline conditions (a beta elimination process), and
d) reduction and stabilizing of terminal aldehyde groups through a reaction with a reducing agent, such as $NaBH_4$.

In a further aspect the method also comprises one or more of the following steps:
e) final purification of the product by means of removing borate (oxidized $NaBH_4$), removal of small glycosaminoglycan fragments, addition of counter-ions and isolation of the product in a solid form.
f) drying of the product under vacuum and heat or as a lyophilization process to enable long term storage of product
g) dissolution and formulation of product in an aqueous phosphate buffered solution, adjustment of pH to 6-8. Addition of excipients for the purpose of tonicity adjustment,
h) aseptic filling of product into vials or syringes or lyophilization in the same In a preferred aspect of the method the chemically modified glycosaminoglycan is unfractionated heparin and unsulfated iduronic and/or unsulfated glucuronic acids is/are selectively oxidized, thereby inhibiting the anticoagulant effect mediated by the interaction between ATIII and the specific pentasaccharide. The oxidation splits an unsulfated uronic acid with 2 vicinal free hydroxyls, at C2 and C3 in the pentasaccharide responsible for AT binding. As a non-limiting example the composition of unfractionated heparin is treated with periodate such as metaperiodate, e.g. unfractionated heparin dissolved in de-ionized water and sodium metaperiodate in suitable proportions. Other oxidation agents would be useful if they have the same chemical impact on oxidation efficacy and on the non-sulfated residues, without affecting other structures or the stability of the final product.

According to a different aspect, the chemically modified glycosaminoglycan according to the invention comprises glycol-split residues with the chemical structure (Formula III):

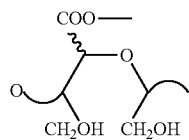

Glycol-split residues appear in polysaccharide chains of the chemically modified heparins, as a result of the oxidation and reduction processes, as earlier discussed in the context with the method and the specific hydrolysis step. The depicted glycol spilt residue arrives from oxidation and reduction of unsulfated iduronic acid and glucuronic acid.

In order to obtain complete oxidation the oxidation step is preferably performed at a temperature of above 10° C., preferably at about 15±2° C., and carried out for at least 15 hours, and preferably for about 18-24 hours.

In the embodiment the periodate oxidation is performed in a solution with an initial glycosaminoglycan (e.g. heparin) concentration of about 10-20% w/v, preferably about 15% w/v. This high concentration of raw material is contributing to a favorable process economy since the precipitation steps subsequently performed in the process are based on volumes of solvent/volume of product.

In a specific embodiment the oxidation step is carried out by the addition of metaperiodate, at a temperature of about 15±2° C., with a glycosaminoglycan (e.g. heparin or heparan sulfate) concentration of about 15% and at a pH of about 5 for about 18-24 hours.

The employment of unfractionated heparin in the process is regarded as generally advantageous for the invention since it will contribute towards reducing waste of material and increasing cost efficacy and support the provision of a composition product with intermediate polysaccharide chain length and favorable bioavailability.

Following periodate oxidation, the methods according to the invention can further comprise at least one step of terminating oxidation and eliminating remaining oxidizing agent. The at least one elimination step includes removing reduced forms of the oxidation agent. In this context reduced forms means oxidation agent transformed to reduced forms contributing to oxidation of targeted saccharide residues in the glycosaminoglycans of the invention. Also in this context, the reducing step can comprise addition of a reducing agent which apart from reducing the oxidized glycosaminoglycan contribute to consume (reduce) remaining oxidizing agent.

Accordingly, the invention is generally directed to a method with the steps of selectively oxidizing an unfractionated glycosaminoglycans, such as heparin or heparan sulfate, by subjecting it to an oxidizing agent capable of oxidizing non-sulfated saccharides; eliminating remaining oxidizing agent and reduced forms of oxidizing agent; and depolymerizing the glycosaminoglycan chains under alkaline condition. For these purposes the elimination step can comprise adding an alcohol, such as an aqueous alcohol; in an amount sufficient for the chemically modified glycosaminoglycan to precipitate. The alcohol can be methanol, propanol, ethanol or similar alcohols and admits the chemically modified glycosaminoglycan to precipitate, while the oxidizing agent and its reduced forms are removed with the alcohol. The precipitation can be performed once or repeated one or several times in order to optimise the removal. However, performing the precipitation only once might be beneficial as it is less time consuming and reduces the exposure time between residual iodine containing compounds and the glycosaminoglycan.

The elimination step can also include addition of a quenching agent capable of chemically inactivating the oxidizing agent to further exert oxidizing effects on the glycosaminoglycan. Any quencher having two vicinal hydroxyl groups can be used. Non-limiting examples of suitable quenchers are ethylene glycol and glycerol. By adding a quencher containing vicinal dihydroxyl groups, periodate is converted to less harmful iodate directly at the end of the oxidation step.

It is generally considered by the inventors that the so described elimination step or elimination steps contribute to counteract or minimize non-specific depolymerization of the glycosaminoglycan, i.e. depolymerization effects not attributable to the predictable results of the alkaline depolymerization process. As mentioned above, non-specific depolymerization may result in unpredictable reduction in molecular weight, discolored products (with increasing absorbance values upon storage), other stability problems and the appearance of unidentified residues not predicted to arrive in glycosaminoglycans such as heparin or low molecular weight heparins.

The introduction of an elimination step enables an improved control over any non-specific depolymerization. Another way of controlling non-specific depolymerization, applicable with any earlier described method, is to reduce the temperature significantly below ambient (room) temperature during the previous precipitation step or steps when adding an alcohol. For example, the temperature can be reduced to about 5° C. in order to prevent from unwanted reactions resulting in non-specific depolymerization.

As an alternative, the process steps a), b) c) and d) are performed in one direct sequence, preferably without any delay. In "direct sequence" in this context means that the steps are performed without any intermediate precipitation step. It is particularly important to minimize the time passing from the end of the oxidation step to the initiation of the reduction step, In one aspect of the invention, the process steps a), b), c) and d) are performed in one direct sequence, preferably without any delay. In "direct sequence" in this context means that the steps are performed without any intermediate precipitation step. In this aspect, the step of eliminating or minimizing the effects of oxidizing iodine compounds comprises controlling the exposure time for any remaining oxidizing iodine compounds to exert any uncontrolled chemical effect on the polysaccharides between the termination of the selective oxidation step and the start of the reduction step.

It is therefore an aspect of the invention to minimize the time passing from the end of the oxidation step to the initiation of the reduction step, i.e. from the onset of the depolymerisation (addition of a base) to the addition of the borohydride. In one aspect the time passing between the end of the oxidation step to the addition of the borohydride is from about 1 hour to about 6 hours. In another aspect the time passing between the end of the oxidation step to the addition of the borohydride is not more than about 5 hours, preferably not more than about 4 hours, more preferable not more than about 3 hours, and most preferable not more than about 2 hours. The minimum time required would be determined of the progress of depolymerization which is controlled by the pH of the reaction. In one aspect the minimum time required is about 1 hour. The lower pH as disclosed for example in Example 3 would result in the longest required time and vice versa for a higher pH. The three steps can advantageously be performed in the same container. This alternative process has the advantage of reducing the exposure time of the heparin or heparan sulfate to the iodine containing compounds from the end of the of the periodate oxidation until they are eliminated by the reducing borohydride in the reduction step. Addition of the borohydride will immediately quench residual periodate and convert it to other, for the product less harmful, inert forms such as iodide and iodine. The borohydride should be added in such an amount to efficiently both quench the residual periodate and reduce terminal aldehyde groups. The positive outcome of compacting the process in this way is demonstrated in Tables II and III.

Following termination of the oxidizing step the polysaccharide chains are depolymerized under alkaline conditions. The de-polymerization is preferably performed at a temperature about 5-25° C. in order to obtain suitably fractionated chains with desirable molecular weights. The pH of the de-polymerizing reaction is between about 10-12, to preserve 2-O-sulfate groups of sulfated uronic acid residues and prevention of increasing yellow coloration of the product at an increasing pH. The latter would impact the shelf life of the product since this is a quality/stability indicator of the product. The requirement to characterize the color as being an indicator of degradation of the product applies. The pH should preferably not reach 13 (0.1N NaOH or higher) due to the risk de-sulfation of 2-O-sulfated uronic acid and even further coloration of the product. The reaction time is preferably about 15-95 minutes to achieve an appropriate reaction with regards to sufficient cleavage of the oxidized non-sulfated uronic acids.

The oxidized glycosaminoglycans are subsequently treated with a reducing agent, for example sodium borohydride, to reduce terminal aldehyde groups. This process is designed to reduce the aldehyde containing end terminals and convert them to primary alcohols to such an extent that the aldehydes would not be detectable by, for example, $^{13}$C-NMR analysis. This high degree of reduction of reducing end terminals contributes to a high stability of the product since aldehydes are inherently chemically labile. Another reason to eliminate the aldehydes is that they may be potentially toxic. Other reducing agents are conceivable if they are capable of performing a similarly specific reducing step of oxidized glucuronic/iduronic acid residues as sodium borohydride without unnecessarily modifying or destroying the sulfate groups of other saccharides. The so reduced chains can be isolated, for example by alcohol precipitation.

In order to support selection of desirable chains, the method can also include a step of enriching heparin or heparan sulfate derivatives in polysaccharide chains having a molecular weight of about from >3 to about 12 kDa. The enrichment step generally includes conventional precipitation, chromatographic, filtering or molecular sieving procedures well known to those skilled in biopolymer manufacturing.

Parameters for the precipitation steps (product concentration, concentration of organic solvent, pH, and additional counter ions) were optimized to retain polysaccharides greater than 3 kDa.

We have developed a high yield novel methodology wherein non-specific depolymerization is minimized. In one aspect simultaneous termination of the oxidation reaction, removal of iodine compounds and precipitation of the modified heparins or heparan sulfates occur. This is advantageous as the iodine compounds which may be detrimental to the product remain soluble in the aqueous ethanol solution and are thereby removed at the precipitation. This is in contrast to earlier methods, for example the method in the U.S. Pat. No. 4,990,502, wherein dialysis or ion exchange is used which are time consuming methods. Dialysis is a cumbersome technique rarely practiced. The sanitation of the equipment would have to be comprehensive to prevent microbial contamination.

In an aspect of the invention, from 4 to 15% of the polysaccharide chains of the chemically modified heparin have a molecular mass of at least 10 kDa.

In an aspect of the invention, from 10 to 25% of the polysaccharide chains of the chemically modified heparin have a molecular mass of at least 8 kDa.

In an aspect of the invention, from 22 to 45% of the polysaccharide chains of the chemically modified heparin have a molecular mass of at least 6 kDa.

In an aspect of the invention, at least 70% of the polysaccharide chains of the chemically modified heparin have a molecular mass of at least 3 kDa.

By performing the process steps according to the present invention a low anticoagulant heparin with a polysaccharide molecular weight specification falling within the distribution disclosed in Table I.

TABLE I

Distribution of polysaccharides and their corresponding molecular mass as cumulative % of weight for several batches.

| Molecular mass, kDa | Cumulative weight, % |
|---|---|
| >10 | 4-15 |
| >8 | 10-25 |
| >6 | 22-45 |
| >3 | >70 |

The corresponding value for weight average molecular weight, Mw, falls in the range 4.6-6.9 kDa.

In one aspect of the invention, the chemically modified glycosaminoglycan has a low, controlled content of chemically modified glucosamine residues as a result of the process steps of its manufacturing.

In one aspect of the invention the chemically modified glycosaminoglycans comprise glucosamines present as signals in the interval of 5.0 to 6.5 of a $^1$H-NMR spectrum with the intensity (% ratio) of less than 4% in relation to the signal at 5.42 ppm from native heparin.

In one aspect, such signals from modified glucosamine signals are present at 6.15 ppm and 5.95 ppm in the $^1$H-NMR spectrum.

In one aspect of the invention, the glycosaminoglycan comprises less than 1% of modified glucosamines of the total glucosamine content. Such modified glucosamines may be located at the non-reducing ends of the polysaccharide chains and may include a C4-C5 double bond in the residue structure. Such modified glucosamines can produce signals at 5.95 ppm and 6.15 ppm in a $^1$H-NMR spectrum.

Chemically modified glucosamines arrive from glucose amine residues liable for modification during production method steps and may contribute to the phenomena discussed with non-specific depolymerization and unpredictable characteristics of the glycosaminoglycan product.

It is an aspect of the invention it is provided a method that minimizes both non-specific depolymerization and the appearance of chemically modified glucosamines by controlling the exposure of the glycosaminoglycans to the agents in the process steps which contribute to modify liable glucosamines.

Accordingly, the inventive methods contribute to minimize modification of liable glucosamines to unpredicted or unknown residues on the polysaccharide chains. The methods thereby contribute to generate products suitably close to heparin or low molecular weight heparin that they may comply with present acceptance criteria for heparin set out by EDQM (European Directorate for the Quality of Medicines & HealthCare), Council of Europe, 2012 (H-NMR Acceptance Criterion).

For this purpose one aspect of the inventive method comprises a step of eliminating or minimizing the effects of the oxidizing agent used to selectively oxidize the glycosaminoglycan. When the oxidizing agent is periodate compound, the elimination step comprises removing reduced forms of the oxidizing agent (iodine compounds).

In one aspect, the step of eliminating or minimizing the effects of oxidizing iodine-containing compounds can comprise controlling the exposure time to any oxidizing agent between the termination of oxidation step to the start of the reduction step.

The so described method yields an overall enrichment of polysaccharide chains with optimal size distribution so as to ensure a product with the desired pharmacological properties, minimized adverse properties, a high bioavailability and handling and storage stability. The method accordingly involves conditions that guarantee complete oxidation and also yields chains with an advantageous size distribution which supports a desirable therapeutic efficacy and is considered to improve the therapeutic index compared to other described low anticoagulant heparins (LANs). The invention does in general terms extend to glycosaminoglycan derivatives prepared with the recited methods.

In another aspect, the present invention is directed to chemically modified heparins or heparan sulfates with an antifactor IIa activity of less than 10 IU/mg, an antifactor Xa activity of less than 10 IU/mg and an average molecular weight (Mw) from about 4.6 to about 6.9 kDa. Such derivatives are possible to produce with method according to the invention. The chemically modified heparins or heparan sulfates according to the invention are further characterized in that:

the polysaccharide chains have from 2 to 20 (n in formula I) disaccharide units corresponding to molecular weights between 1.2 and 12 kDa;
the predominantly occurring disaccharide is (Formula I)

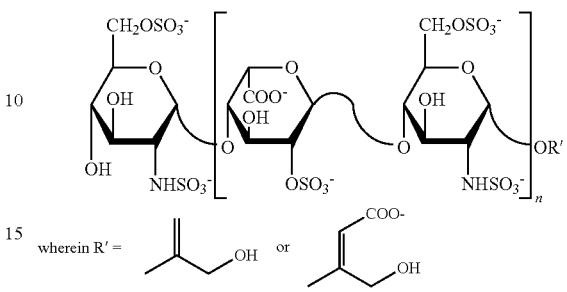

n is an integer from 2 to 20.

The predominant disaccharide has a molecular weight of about 600 Da. The term "predominantly" does in this context have the meaning of "the frequently most present" polysaccharide chains.

Further, in glycosaminoglycans modified according to the above disclosed method the polysaccharide chains retain at least 70%, preferably at least 80%, more preferably at least 90%, and even more preferably essentially all of the sulfate groups of the corresponding native glycosaminoglycan. It is another characterizing feature that the polysaccharide chains essentially lack chemically intact pentasaccharide sequences mediating the anticoagulant effect, when compared to the chains of the corresponding native glycosaminoglycan.

Further, in the modified glycosaminoglycans according to the invention, the predominant size is 6-12 disaccharide units corresponding to molecular weights of 3.6-7.2 kDa. The term "predominantly" does in this context have the meaning of "the frequently most present" polysaccharide chains.

In one aspect of the invention the chemically modified glycosaminoglycan is essentially free of intact non-sulfated iduronic and/or glucuronic acids. Essentially free in this context means not detectable in a $^{13}$C-NMR spectrum. Typically the detection limit is set to 0.1%.

It is also preferred that the modified glycosaminoglycans are derived from heparin and that the chains are essentially free of non-sulfated iduronic and/or non-sulfated glucuronic acids, preferably D-glucuronic acid resulting in deletion of chemically intact pentasaccharides mediating the anticoagulant effect, when compared to the chains of corresponding native heparin.

It is further preferred that the chemically modified glycosaminoglycans comprise chains with reducing end terminals alternatives R' as disclosed in FIG. 1. The non-reducing terminals are predominantly GlcN, sulfated glucosamines.

It is also preferred that the chemically modified glycosaminoglycans have at least 70% of the polysaccharide chains with a molecular weight above 3 kDa. It is also suitable that less than 5%, preferably less than 3% and more preferably less than 1% of the polysaccharide chains have a molecular weight above 15 kDa.

Preferably the chemically modified sulfated heparins of the invention have molecular weight averages that are stable for at least 36 months at 5° C. as an aqueous phosphate buffered solution, preferably for at least 48 months and more preferably for at least 60 months. The molecular weight average remains stable when stored as a powder for at least 5 years at a temperature of 25° C. Further details on the stability characteristics can be found in example 2.

The present invention also relates to chemically modified glycosaminoglycans produced with the method disclosed above.

The invention further relates to pharmaceutical compositions, useful in treating the mentioned complications and preferred therapeutic embodiments, comprising therapeutically effective amounts of the described chemically modified glycosaminoglycans and a therapeutically acceptable carrier. Such compositions can be administered systemically by parenteral administration, such as by subcutaneous or intravenous injection. The pharmaceutical compositions may also be given by oral administration. For parenteral administration the active compounds can be incorporated into a solution or suspension, which also contain one or more adjuvants such as sterile diluents such as water for injection, saline, fixed oils, polyethylene glycol, glycerol, propylene glycol or other synthetic solvents, antibacterial agents, antioxidants, chelating agents, buffers and agents for adjusting the osmolality. The parenteral preparation can be delivered in ampoules, vials, disposable syringes or as infusion arrangements, also for self administration.

The modified glycosaminoglycans according to the invention are well adapted for subcutaneous administration and thereby with suitable self-administration tools, such as injectors, since they have a molecular weight distribution favorable for resorption from a subcutaneous depot and in this way resemble commercially available low molecular weight heparins.

Further, due to the favorable molecular weight distribution, the modified glycosaminoglycans according to the invention are well suited for topical administration, including penetration of mucus membranes such as, but not limited to, vaginal, rectal, intra uterine, and nasal administration.

The present invention also relates to chemically modified glycosaminoglycans as described above for use in medical treatments not dependent on an anticoagulant effect.

The present invention further relates to the use of a chemically modified glycosaminoglycan according to the invention for the manufacture of a medicament for medical treatments not dependent on an anticoagulant effect.

Non-limiting examples of such medical treatments are prevention and treatment of protracted labor (dystocia) and protein leakage in for example Gorham Stout syndrome. Protein leakage from endothelial or epithelial linings also occurs in disorders such as sepsis and protein-losing enteropathy. The chemically modified glycosaminoglycans according to the invention are administered to the patient in a therapeutically effective amount.

LMWH as well as low anticoagulant heparin augment oxytocin induced myometrial contractility both in vitro and in vivo in term pregnant women. Addition of LMWH or low anticoagulant heparin according to the invention to cervical cell culture raised from human cervical biopsies sampled at vaginal delivery increases the synthesis of interleukin-6 and -8. This finding supports LMWH and low anticoagulant heparin to induce cervical ripening. Thus LMWH and low anticoagulant heparin has an inflammatory action in the cervix in opposition to its documented anti-inflammatory effect in other organs. Thus, the chemically modified GAG according to the invention can be used for prevention and treatment of protracted labor.

It has been hypothesized that the administration of low anticoagulant heparin to a patient will decrease the ability of proteins to pass through the cellular barrier and thereby treat or prevent protein leakage from endothelial or epithelial linings. It is further hypothesized that the low anticoagulant heparin as defined above bind factors such as cytokines and growth factors (such as VEGF) and thereby modulate the activity of these factors. Another such factor, heparin-binding protein (HBP, azurocidin) is involved in endothelial leakage and was recently suggested to be the prime marker of early sepsis. Given the fact that HBPs seem to be involved in both the pathological angiogenic process in for example Gorham stout syndrome and in conditions with leaky vessels (HBP), and that loss of heparan sulfate can lead to leakage of proteins over the intestinal epithelium, it is hypothesized that giving a low anticoagulant heparin according to the invention in conjunction with more conventional therapies, would be beneficial and that the heparin will slow the process down. (*Acta Paediatrica* 2011 100, pp. 1448-1453).

In summary, the in-vivo effect of the chemically modified glycosaminoglycans according to the invention derives from a combination of suitable molecular weight distribution and strong polyanionic properties. The inventive process has been optimized, scaled up and produced according to GMP, allowing the product to be administered to humans.

The invention will now be further described in the following non-limiting examples.

EXAMPLES

Detailed Description of the Manufacturing Process of a Chemically Modified Heparin According to the Invention The substance is prepared from Heparin Sodium. The preparation involves selective oxidation of non-sulfated uronic acid residues in heparin by periodate, including the glucuronic acid moiety in the pentasaccharide sequence that binds AT. Disruption of the structure of this residue annihilates the high-affinity interaction with AT and, consequently, the anticoagulant effect (measured as a-FXa or a-FIIa) is essentially depleted. Subsequent alkaline treatment, beta-elimination reaction results in cleavage of the polymer at the sites of non-sulfated uronic acids that have been oxidized by periodate. Together, these manipulations lead to a loss of anticoagulant activity along with adequate de-polymerization of the heparin chain.

Further, the resulting reducing end terminal at the site of cleavage is reduced by $NaBH_4$, which converts the terminal aldehyde to the corresponding diols which are more stable. Subsequently, additives, impurities and side-products are removed by repeated precipitations with ethanol, filtration and centrifugations. Thereafter the substance is obtained in powder form by drying with vacuum and heat. The drug substance will be dissolved in a sterile aqueous buffer to yield the drug product, which is intended for intravenous or subcutaneous administration.

The processes so far described generally include the steps of oxidation, polymer cleavage (alkaline hydrolysis) and reduction. The processes according to the present invention are developed in order to counteract or eliminate any type of non-specific depolymerization of the heparin chains. Non-specific polymerization in this context means generally such depolymerization that is not related to the specific alkaline beta-elimination reaction. Non-specific depolymerization results in structural instabilities of the product that may result in further depolymerisation and discoloration during storage of the purified product. In addition, it may contribute to the appearance of atypical species appearing in NMR spectra not normally found in heparin.

The processes described and exemplified in the following section include different aspects of counteracting or eliminating non-specific depolymerization.

Example 1

Oxidation of Non-Sulfated Glucuronic- and Iduronic Acid (Residues), Deletion of AT-Binding Pentasaccharide and Anticoagulant Activity A quantity of about 3000 grams of Heparin is dissolved in purified water to obtain a 10-20% w/v solution. The pH of this solution is adjusted to 4.5-5.5. The sodium metaperiodate ($NaIO_4$) is subsequently added to the process solution; quantity of periodate 15-25% of the weight of heparin. The pH is again adjusted to 4.5-5.5. The reaction is protected from light. The process solution is reacted during the 18-24 hours with constant stirring maintenance of the temperature at 13-17° C., while the temperature is reduced to 5° C. during the last two hours.

Termination of the Oxidation Reaction and Removal of Iodine-Containing Compounds Ethanol (95-99.5%) is added to the reaction mixture over a period of 0.5-1 hour, with careful stirring and at a temperature of 5-25° C. The volume of ethanol to be added is in the range 1-2 volumes of ethanol per volume of process solution. The oxidized heparin is then allowed to precipitate and sediment for 15-20 hours, after which the mother liquor is decanted and discarded.

Next, the sediment is dissolved in purified water to obtain a 15-30% w/v process solution. NaCl is added to obtain a concentration of 0.15-0.30 mol/liter in the process solution. Stirring continues for another 0.5-1 hour while maintaining the temperature of 5-25° C. Subsequently 1.0-2.0 volumes of ethanol (95-99.5%) per volume of process solution are added to this solution with stirring, during a period of 0.5-1 hour. This precipitates the product from the solution.

De-Polymerization of Polysaccharide Chains by an Alkaline Beta Elimination Process After the mother liquor has been decanted and discarded, the sediment is stirred in approximately 7 liters of water until completely dissolved, the concentration of the solution is now 15-30%. While maintaining the temperature at 5-25° C. a 4 M NaOH solution is added slowly until a pH of 10.5-12 is obtained. The reaction is initiated and proceeds for 15-95 minutes. At this time, the pH of the solution is recorded and 4 M HCl is added slowly until a pH of 5.5-7 is obtained.

Reduction of Reducing End Terminals

While maintaining the temperature at 13-17° C., the pH of the solution is adjusted to 5.5-6.5. A quantity of 130-150 grams of sodium borohydride is then added to the solution while the pH will increase to 10-11, the reaction is continued for 14-20 hours. After this reaction time, a dilute acid is added slowly in order to adjust the pH to a value of 4, this degrades remaining sodium borohydride. After maintaining a pH of 4 for 45-60 minutes, the pH of the solution is adjusted to 7 with a dilute NaOH solution.

The purification continues according to example 5

Example 2

Oxidation of Glucuronic and Iduronic Acid (Residues), Deletion of Anticoagulant Activity A quantity of about 3000 grams of Heparin is dissolved in purified water to obtain a 10-20% w/v solution. The pH of this solution is adjusted to 4.5-5.5. The sodium metaperiodate ($NaIO_4$) is subsequently added to the process solution; quantity of periodate 15-25% of the weight of heparin. The pH is again adjusted to 4.5-5.5. The reaction is protected from light. The process solution is reacted during the 22-26 hours with constant stirring and maintenance of the temperature at 13-17° C., while the temperature is reduced to 5° C. during the last two hours. The pH at the end of the reaction period is measured and recorded.

Termination of the Oxidation Reaction and Removal of Iodine-Containing Compounds Ethanol (95-99.5%) is added to the reaction mixture over a period of 0.5-1 hour, with careful stirring and at a temperature of 5-25° C. The volume of ethanol to be added is in the range 1-2 volumes of ethanol per volume of process solution. The oxidized heparin is then allowed to precipitate and sediment for 15-20 hours, after which the mother liquor is decanted and discarded.

De-Polymerization of Polysaccharide Chains by an Alkaline Beta Elimination Process After the mother liquor has been decanted and discarded, the sediment is stirred in approximately 7 liters of water until it appears visually to be completely dissolved. While maintaining the temperature at 20-25° C. 4 M NaOH is added slowly until a pH of 10.5-12 is obtained and the reaction thus initiated is allowed to proceed for 15-95 minutes. At this time, the pH of the solution is recorded and 4 M HCl is added slowly until a pH of 5.5-7 is obtained.

Reduction of Reducing End Terminals

After the mother liquor has been decanted and discarded, the sediment is dissolved by addition of purified water until a concentration of the process solution of 15-30% w/v is obtained. While maintaining the temperature at 13-17° C., the pH of the solution is adjusted to 5.5-6.5. A quantity of 130-150 grams of sodium borohydride is then added to the solution and dissolved, the pH will immediately increase to a pH of 10-11, the reaction is continued for 14-20 hours. The pH of the solution, both prior to and after this reaction period, is recorded. After this reaction time, a dilute acid is added slowly in order to adjust the pH to a value of 4, this degrades remaining sodium borohydride. After maintaining a pH of 4 for 45-60 minutes, the pH of the solution is adjusted to 7 with a dilute NaOH solution.

Purification continues according to Example 5.

Example 3

Oxidation of Glucuronic and Iduronic Acid (Residues), Deletion of Anticoagulant Activity A quantity of about 3000 grams of Heparin is dissolved in purified water to obtain a 10-20% w/v solution. The pH of this solution is adjusted to 4.5-5.5. The sodium metaperiodate ($NaIO_4$) is subsequently added to the process solution, quantity of periodate 15-25% of the weight of heparin. The pH is again adjusted to 4.5-5.5. The reactor is protected from light. The process solution is reacted during the 18-24 hours with constant stirring maintenance of the temperature at 13-17° C., while the temperature is reduced to 5° C. during the last two hours.

De-Polymerization of Polysaccharide Chains by an Alkaline Beta Elimination Process While maintaining the temperature at 5-25° C., 4 M NaOH solution is added slowly until a pH of 10.5-12 is obtained. The reaction is initiated and proceeds for 15-95 minutes. At this time, the pH of the solution is recorded and 4 M HCl is added slowly until a pH of 5.5-7 is obtained.

Reduction of Reducing End Terminals

While maintaining the temperature at 13-17° C., the pH of the solution is adjusted to 5.5-6.5. A quantity of 130-200 grams of sodium borohydride is then added to the solution while the pH will increase to 10-11, the reaction is continued for 14-20 hours. After this reaction time, a dilute acid is added slowly in order to adjust the pH to a value of 4, this degrades remaining sodium borohydride. After maintaining a pH of 4 for 45-60 minutes, the pH of the solution is adjusted to 7 with a dilute NaOH solution.

Precipitation of Reduced Product and Initial Removal of Iodine-Containing Compounds Ethanol (95-99.5%) is added to the reaction mixture over a period of 0.5-1 hour, with careful stirring and at a temperature of 5-25° C. The volume of ethanol to be added is in the range 1-2 volumes of ethanol per volume of process solution. The oxidized heparin is then allowed to precipitate and sediment for 15-20 hours, after which the mother liquor is decanted and discarded.

Next, the sediment is dissolved in purified water to obtain a 15-30% w/v process solution. NaCl is added to obtain a concentration of 0.15-0.30 mol/liter in the process solution Purification continues according to Example 5.

Example 4

Oxidation of Glucuronic and Iduronic Acid (Residues), Deletion of Anticoagulant Activity A quantity of about 3000 grams of Heparin is dissolved in purified water to obtain a 10-20% w/v solution. The pH of this solution is adjusted to 4.5-5.5. The sodium metaperiodate ($NaIO_4$) is subsequently added to the process solution, quantity of periodate 15-25% of the weight of heparin. The pH is again adjusted to 4.5-5.5. The reactor is protected from light. The process solution is reacted during the 18-24 hours with constant stirring maintenance of the temperature at 13-17° C., while the temperature is reduced to 5° C. during the last two hours. Next, glycerol is added to quench the reaction, i.e. to convert residual periodate to iodate, 150-200 ml of a 85% glycerol solution is added and reacted for 30-60 minutes while stirring.

Precipitation of Product Removal of Iodine-Containing Compounds and Quencher/Reaction Products Ethanol (95-99.5%) is added to the reaction mixture over a period of 0.5-1 hour, with careful stirring and at a temperature of 5-25° C. The volume of ethanol to be added is in the range 1-2 volumes of ethanol per volume of process solution. The oxidized heparin is then allowed to precipitate and sediment for 15-20 hours, after which the mother liquor is decanted and discarded.

Next, the sediment is dissolved in purified water to obtain a 15-30% w/v process solution. NaCl is added to obtain a concentration of 0.15-0.30 mol/liter in the process solution. Stirring continues for another 0.5-1 hour while maintaining the temperature of 5-25° C. Subsequently 1.0-2.0 volumes of ethanol (95-99.5%) per volume of process solution are added to this solution with stirring, during a period of 0.5-1 hour. This precipitates the product from the solution.

De-Polymerization of Polysaccharide Chains by an Alkaline Beta Elimination Process After the mother liquor has been decanted and discarded, the sediment is stirred in approximately 7 liters of water until it appears visually to be completely dissolved. While maintaining the temperature at 5-25° C. 4 M NaOH is added slowly until a pH of 10.5-12 is obtained and the reaction thus initiated is allowed to proceed for 60-95 minutes. At this time, the pH of the solution is recorded and 4 M HCl is added slowly until a pH of 5.5-7 is obtained.

Reduction of Reducing End Terminals

After the mother liquor has been decanted and discarded, the sediment is dissolved by addition of purified water until a concentration of the process solution of 15-30% w/v is obtained. While maintaining the temperature at 13-17° C., the pH of the solution is adjusted to 5.5-6.5. A quantity of 130-150 grams of sodium borohydride is then added to the solution and dissolved, the pH will immediately increase to a pH of 10-11, the reaction is continued for 14-20 hours. The pH of the solution, both prior to and after this reaction period, is recorded. After this reaction time, a dilute acid is added slowly in order to adjust the pH to a value of 4, this degrades remaining sodium borohydride. After maintaining a pH of 4 for 45-60 minutes, the pH of the solution is adjusted to 7 with a dilute NaOH solution.

Purification proceeds according to Example 5.

Example 5

Purification of the Product

Removal of Process Additives and Impurities, Addition of Counter-Ions and Filtration Process solutions according to Examples 1-4 arriving from the final chemical modification step of reducing the end terminals by borohydride is worked up according the methodologies outlined below.

One volume of process solution is then added to 1.5-2.5 volumes of ethanol (95-99.5%) followed by centrifugation at >2000 G, at <20° C. for 20-30 minutes, after which the supernatant is decanted and discarded.

The product paste obtained by centrifugation is then dissolved in purified water to obtain a product concentration 10-20% w/v. Then NaCl is added to obtain a concentration of 0.20-0.35 mol/liter. Next 1.5-2.5 volumes of ethanol (95-99.5%) are added per volume of process solution which precipitates the product from the solution. Centrifugation follows as described above Next the remaining paste is added purified water to dissolve. The product concentration would now be in the range of 10-20% w/v. The pH of the product solution is now adjusted to 6.5-7.5. The solution is then filtered to remove any particulates. Then, to one volume of process solution is added 1.5-2.5 volumes of ethanol (95-99.5%). Centrifugation follows at >2000 G, and at <20° C. for 20-30 minutes after which the supernatant is decanted and discarded.

Dewatering of Precipitate Paste and Reduction of Particle Size.

A reactor is filled with ethanol, volume about 2 liters. While stirring the ethanol, the precipitate paste is added. The mechanical stirring solidifies the paste and replaces the water present by the ethanol giving a homogenous particle suspension. The stirring is discontinued after 1-2 hours after which the particles are allowed to sediment. After removal of excessive liquid, the particles are passed through a sieve or a mill to obtain smaller and uniform sized particles.

Drying of Product

The product is distributed evenly onto trays, and placed in a vacuum cabinet. Vacuum is applied and heating is performed at 35-40° C. A stream of nitrogen is passed through the drier at this time while maintaining the low pressure in the dryer. When a constant weight is obtained of the product, i.e. no further evaporation is noticed, the drying is considered complete. The product is packed and protected from humidity.

Example 6

Oxidation of Glucuronic and Iduronic Acid (Residues), Deletion of Anticoagulant Activity A quantity of about 3000 grams of Heparin is dissolved in purified water to obtain a 10-20% w/v solution. The pH of this solution is adjusted to 4.5-5.5. The sodium metaperiodate ($NaIO_4$) is subsequently added to the process solution, quantity of periodate 15-25% of the weight of heparin. The pH is again adjusted to 4.5-5.5. The reaction is protected from light. The process solution is reacted during the 18-24 hours with constant stirring maintenance of the temperature at 13-17° C., while the temperature is reduced to 5° C. during the last two hours.

De-Polymerization of Polysaccharide Chains by an Alkaline Beta Elimination Process While maintaining the temperature at 5-25° C. 4 M NaOH is added slowly until a pH of 10.5-12 is obtained and the reaction thus initiated is allowed to proceed for 15-95 minutes. At this time, the pH of the solution is recorded and 4 M HCl is added slowly until a pH of 5.5-7 is obtained.

Reduction of Reducing End Terminals

After the mother liquor has been decanted and discarded, the sediment is dissolved by addition of purified water until a concentration of the process solution of 15-30% w/v is obtained. While maintaining the temperature at 13-17° C., the pH of the solution is adjusted to 5.5-6.5. A quantity of 130-200 grams of sodium borohydride is then added to the solution and dissolved, the pH will immediately increase to a pH of 10-11, the reaction is continued for 14-20 hours. The pH of the solution, both prior to and after this reaction period, is recorded. After this reaction time, a dilute acid is added slowly in order to adjust the pH to a value of 4, this degrades remaining sodium borohydride. After maintaining a pH of 4 for 45-60 minutes, the pH of the solution is adjusted to 7 with a dilute NaOH solution. Purified water is now added to the solution until a conductivity of 15-20 mS/cm is obtained of the reaction solution.

Purification of Product by Anion Exchange Chromatography

A column with a diameter 500 mm is packed with media, DEAE-Sepharose or QAE-Sepharose to a volume of 25-30 liters corresponding to a bed height of 10-15 cm. The chromatography is performed in 3-4 cycles to consume all the product.

Next buffers are prepared,

Equilibration buffer, Buffer A, 15 mM phosphate, 150 mM NaCl

Elution buffer, Buffer B, 2 M NaCl solution

Sanitation buffer, 0.5 M NaOH

The chromatography step is performed at 15-25° C., at flow rate of <200 cm/hour or approx. 350 liters/hour.

The column is equilibrated with the equilibration buffer until the eluent has a conductivity of 15-20 mS/cm. Next the oxidized heparin solution is pumped into the column. The quantity of crude product to be applied corresponds to <40 g/liter of chromatography media.

An isocratic wash follows with equilibration buffer and is discontinued when the UV 210-254 nm has reached a baseline. Typically 5 bed volumes of buffer are required to reach baseline. Chemicals added to the process and products formed of these are removed.

Next, the ionic strength of the buffer applied onto the column is linearly increased by performing a gradient elution. The Buffer A decreases from 100% to 0% replaced by 100% Buffer B over 5 bed volumes. The product, eluate is collected when the UV absorbance is >0.1 AU and is discontinued when the signal is <0.1 AU. Sanitation of the column is then performed after which it is again prepared for the next cycle of chromatography. Eluates from all runs are combined and stored at 15-25° C.

De-Salting of the Product

One volume of the combined eluates from previous step is added 3 volumes of 95-99.5% ethanol, 15-25° C., under constant stirring. This precipitates the product out of solution. The product is allowed to sediment for >3 hours. Next, the sediment is dissolved in purified water to a concentration of 15-25%. The solution is now added to cold ethanol (<-5° C.) 95-99.5%, typically 5 volumes of ethanol per one volume of product solution are consumed. Next follows centrifugation in a continuous mode, >2000 G, the product paste is thereafter collected and prepared for drying.

Drying of Product

The product is distributed evenly onto trays, and placed in a vacuum cabinet. Vacuum is applied and heating is performed at 35-40° C. A stream of nitrogen is passed through the drier at this time while maintaining the low pressure in the dryer. When a constant weight is obtained of the product, i.e. no further evaporation is noticed, the drying is considered complete. The product is milled and made homogenous, thereafter packed and protected from humidity.

Example 8

Low anticoagulant heparin produced according to the examples 1 and 3 was subjected to 1H-NMR analysis and compared to the spectrum of native heparin.

Table II demonstrates signals in the interval 5.00 ppm to 6.50 ppm not present in native heparin generated from non-reducing end unsaturated glucosamines. The results of Table II show that it is possible to reduce the presence of such compounds not predicted to be present in spectrum from native heparin to low levels. In comparison, the current limit applicable to heparin quality control, monograph 7, EDQM is <4% compared to the signal at 5.42 ppm for any signal in the region 5.70-8.00 ppm.

TABLE II

Qualitative results of a low anticoagulant heparin with regards to unusual signals. Signal intensity for signals 6.15 and 5.95 ppm in a 1H-NMR spectra

| | | Intensity (% ratio) to 5.42 ppm signal of a native heparin following EDQM, monograph 7 | |
|---|---|---|---|
| Sample | Production method | 6.15 ppm % of ref. signal | 5.95 ppm % of ref. signal |
| Batch 1 | Example 1 | 11 | 12 |
| Batch 2 | Example 1 | 13 | 16 |
| Batch 3 | Example 3 | 2 | 2 |

Further, the presence of non reducing end unsaturated glucosamines was also quantified by combined 1H-NMR and 13C-NMR spectra evaluation (HSQC) and demonstrated as mol % of total glucosamines (see Table III).

Furthermore, the sample was analyzed by following the NMR two-dimensional (2D) method involving the combined use of proton and carbon NMR spectroscopy (HSQC)

as previously described (see Guerrini M., Naggi A., Guglieri S, Santarsiero R, Torri G. Anal Biochem 2005; 337, 35-47.)

Table III demonstrates the fraction (%) of modified glucosamines compared to the total amount of glucosamines of the low anticoagulant heparin as present as signals at 5.95 ppm and 6.15 ppm in the $^1$H-NMR spectrum.

TABLE III

Results from quantitative determination of unusual signals 5.95 ppm, 6.15 ppm of total glucosamine

| Sample | Production method | 6.15 ppm signal mol % of glucosamine | 5.95 ppm signal mol % of glucosamine |
|---|---|---|---|
| Batch 1 | Example 1 | 6 | 3 |
| Batch 2 | Example 3 | <1 | <1 |

Example 9

The product manufactured according to any one of the examples above can prepared as drug product by a conventional aseptic process, such as solution comprising 150 mg/mL of active product and Na phosphate to 15 mM, pH 6-8. The so obtained drug product is intended primarily for subcutaneous administration but suitable for intra-venous administration.

The resulting product is a depolymerized form of heparin with a projected average molecular weight of 4.6-6.9 kDa and with essentially no anticoagulant activity.

The product has a size distribution of polysaccharide polymers, with a range for n of 2-20 corresponding to molecular weights of 1.2-15 kDa. The predominant size is 6-16 disaccharide units corresponding to molecular weights of 3.6-9.6 kDa.

The molecular weight was determined by GPC-HPLC carried out with a TSK 2000 and TSK 3000 SW columns in series. Refractive index was used for evaluation. First international calibrant for LMWH was used.

Below is presented the molecular mass distribution and the corresponding part of the cumulative percentage of total weight.

TABLE IV

Distribution of polysaccharides and their corresponding molecular mass in as cumulative % of weight for several batches

| Molecular mass, kDa | Cumulative weight, % |
|---|---|
| >15 | <1 |
| >10 | 4-15 |
| >9 | 7-20 |
| >8 | 10-27 |
| >7 | 15-35 |
| >6 | 22-45 |
| >5 | 34-56 |
| >4 | 47-70 |
| >3 | >70 |
| >2 | >85 |

The corresponding value for weight average molecular weight, Mw falls in the range 4.6-6.9 kDa Example 10

The stability of the drug substance (powder) and drug product dissolved in aqueous phosphate buffered solution of a chemically modified GAG produced according to the inventive method was studied. The results are disclosed in Tables V and VI below.

TABLE V

Results from stability on Drug Substance over 60 months. Based on selected stability indicating parameters.

| Test | | Appearance Visual | Colour Absorbance of a 10% solution, 400 nm | Average Molecular weight Mw, kDa | pH |
|---|---|---|---|---|---|
| Storage conditions: | | | | | |
| Temp(° C.)/% RH | Time (months) | | | | |
| | Initial | White to slightly yellow powder | 0.09 | 5.5 | 8.8 |
| 25/60 | 3 | Complies | 0.10 | 5.7 | 8.9 |
| | 6 | Complies | 0.11 | 5.5 | 8.6 |
| | 12 | Complies | 0.10 | 5.5 | 8.8 |
| | 18 | Complies | 0.10 | 5.5 | 8.4 |
| | 24 | Complies | 0.10 | 5.5 | 8.7 |
| | 36 | Complies | 0.11 | 5.5 | 8.4 |
| | 48 | Complies | 0.12 | 5.5 | 8.1 |
| | 60 | Complies | 0.11 | 5.5 | 8.3 |

TABLE VI

Results from stability on Drug Product over 36 months based on selected stability indicating parameters.

| Test | Appearance | Colour, absorbance at 400 nm 10% w/v solution | pH | Osmolality mOsm/kg | Average Molecular weight Mw kDa | Assay Content mg/mL |
|---|---|---|---|---|---|---|
| Storage conditions: | | | | | | |
| Temp(° C.)/% RH | Time (months) | | | | | |
| Initial | Clear white to slight yellow solution free of visible particles | 0.14 | 7.0 | 658 | 5.6 | 150 |
| 5/Ambient | 1 | Complies | 0.10 | 7.0 | 658 | 5.4 | 155 |
| | 3 | Complies | 0.11 | 7.0 | — | 5.4 | — |
| | 6 | Complies | 0.12 | 7.1 | 637 | 5.5 | 147 |
| | 9 | Complies | 0.12 | 7.1 | — | 5.5 | — |
| | 12 | Complies | 0.13 | 7.0 | 648 | 5.5 | 156 |
| | 18 | Complies | 0.12 | 7.1 | 660 | 5.4 | — |
| | 24 | Complies | 0.12 | 71 | 658 | 5.4 | 152 |
| | 36 | Complies | 0.13 | 71 | 657 | 5.4 | 153 |

Example 11

Subcutaneous Administration

Tritium labeled chemically modified heparin produced by the method disclosed in example 1 was administered to Sprauge Dawley rats and dogs.

Results:

Following subcutaneous administration at 2, 8 and 24 mg heparin/kg/day in the rat and 3, 15 and 45 mg heparin/kg/day in the dog, absorption was rapid and maximal plasma levels were generally reached within 0.5 and 1.5 h in the rat and dog, respectively. The subcutaneous bioavailability was around 90% in both the rat and the dog. Interestingly, the corresponding bioavailability for heparin is about 10%.

Although particular embodiments have been disclosed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the spirit and scope of the invention as defined by the claims.

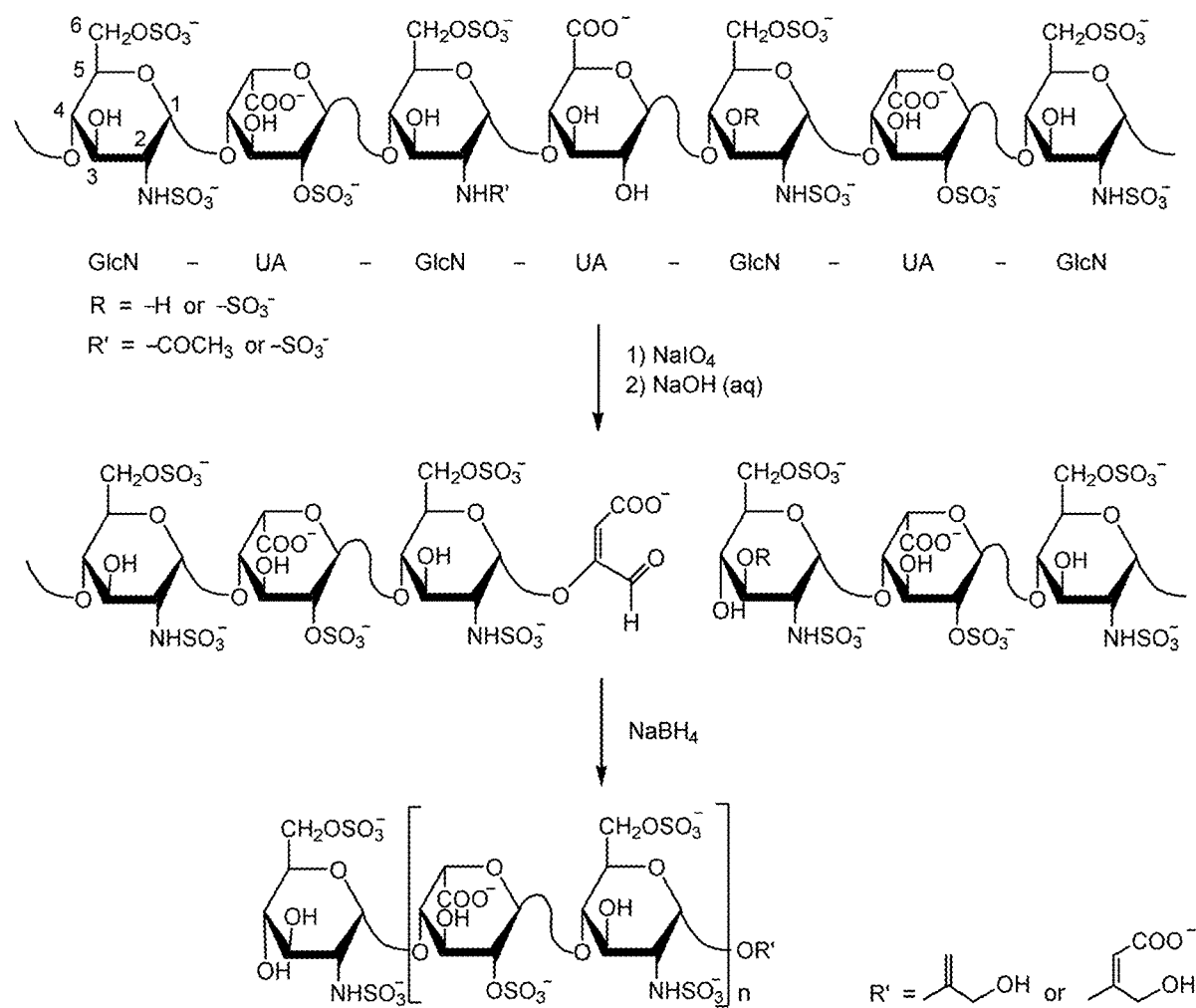

The invention claimed is:

1. A chemically modified glycosaminoglycan, which glycosaminoglycan is selected from the group consisting of heparin and heparan sulfate, which chemically modified glycosaminoglycan has an antifactor IIa activity and an antifactor Xa activity, with the antifactor IIa activity being less than 10 IU/mg and the antifactor Xa activity being less than 10 IU/mg, the chemically modified glycosaminoglycan having a weight average molecular weight (Mw) from about 4.6 to about 6.9 kDa, and wherein, in the chemically modified glycosaminoglycan:

the polysaccharide chains have from 2 to 20 disaccharide units corresponding to molecular weights between 1.2 and 12 kDa;

the polysaccharide chains are essentially free of chemically intact non-sulfated iduronic and/or glucuronic acids from pentasaccharide sequences mediating the anticoagulant effect of heparin and heparin sulfate;

the predominantly occurring disaccharide is (Formula I)

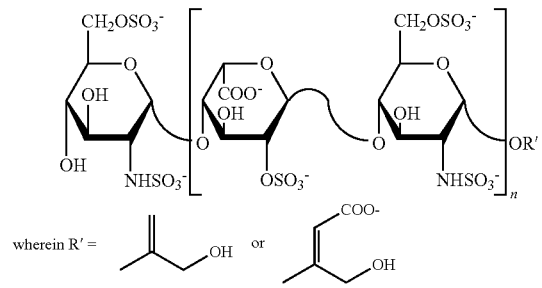

n is an integer from 2 to 20; and the distribution of molecular weights of the polysaccharides in the chemically modified glycosaminoglycan are expressed as cumulative % of weight according to the following table:

| Molecular mass, kDa | Cumulative weight, % |
|---|---|
| >10 | 4-15 |
| >8 | 10-25 |
| >6 | 22-45 |
| >3 | >70. |

2. The chemically modified glycosaminoglycan according to claim 1, wherein the predominantly occurring polysaccharide chains have between 6 and 12 disaccharide units with molecular weights from 3.6-7.2 kDa.

3. The chemically modified glycosaminoglycan according to claim 1, wherein the chemically modified glycosaminoglycan is essentially free of intact non-sulfated iduronic and/or glucuronic acids.

4. The chemically modified glycosaminoglycan according to claim 1, wherein the chemically modified glycosaminoglycan is heparin.

5. A method of preparing a chemically modified glycosaminoglycan selected from the group consisting of heparin and heparan sulfate which chemically modified glycosaminoglycan has an antifactor IIa activity and an antifactor Xa activity, with the antifactor IIa activity being less than 10 IU/mg and the antifactor Xa activity being less than 10 IU/mg, the chemically modified glycosaminoglycan having a weight average molecular weight (Mw) from about 4.6 to about 6.9 kDa, the method comprising the sequential steps of:
- (a) oxidation of glucuronic and iduronic acids by treatment with periodate,
- (b) eliminating or minimizing the effects of oxidizing iodine-containing compounds,
- (c) depolymerization of polysaccharide chains under alkaline conditions, and
- (d) reduction and stabilizing of terminal aldehyde groups through a reaction with a reducing agent;

wherein step b)
- (i) is performed by precipitation which is accomplished by addition of ethanol; or
- (ii) comprises ensuring that the amount of time that elapses between the end of step a) and the start of step d) is not more than about 6 hours; or
- (iii) is performed by addition of a quencher compound comprising two vicinal hydroxyl groups.

6. The method according to claim 5, wherein step b) is performed by precipitation which is accomplished by addition of ethanol.

7. The method according to claim 5, wherein step b) comprises ensuring that the amount of time that elapses between the end of step a) and the start of step d) is not more than about 6 hours.

8. The method according to claim 5, wherein step b) is performed by addition of a quencher compound comprising two vicinal hydroxyl groups.

9. The method according to claim 5, wherein the periodate oxidation is performed at a temperature of above 10° C.

10. The method according to claim 5, wherein the periodate oxidation is performed in a solution with an initial glycosaminoglycan concentration of about 10-20% w/v.

11. The method according to claim 5, wherein the oxidation process is carried out for at least 15 hours.

12. The method according to claim 5, wherein the periodate oxidation is performed at a temperature of about 15±2° C., with a glycosaminoglycan concentration of about 15% and at a pH about 5 for about 18-24 hours.

13. The method according to claim 5 wherein depolymerizing is performed at a temperature above about 20° C.

14. The method according to claim 5, wherein said method is effective to enrich glycosaminoglycan derivatives in polysaccharide chains having a molecular weight of from about 1.2 to about 12 kDa.

15. The method according to claim 5, wherein the glycosaminoglycan is heparin.

16. A chemically modified glycosaminoglycan, produced to the method of claim 5, wherein the chemically modified glycosaminoglycan is essentially free of chemically intact non-sulfated iduronic and/or glucuronic acids of native heparin, and comprises a distribution of molecular weights of polysaccharides which are expressed as cumulative % of weight according to the following table:

| Molecular weight, kDa | Cumulative weight, % |
|---|---|
| >10 | 4-15 |
| >8 | 10-25 |
| >6 | 22-45 |
| >3 | >70. |

17. The chemically modified glycosaminoglycan according to claim 1, wherein the molecular weight average is stable for at least 36 months at 5° C. as an aqueous phosphate buffered solution.

18. The chemically modified glycosaminoglycan according to claim 1, wherein the molecular weight average remains stable when stored as a powder for at least 5 years at a temperature of 25° C.

19. A pharmaceutical composition, comprising a therapeutically effective amount of the chemically modified sulfated glycosaminoglycan according to claim 1 and a pharmaceutically acceptable carrier.

20. A method for the treatment of dystocia wherein the chemically modified glycosaminoglycan according to claim 1 is administered to a patient in a therapeutically effective amount.

21. A method for the treatment of sepsis wherein the chemically modified glycosaminoglycan according to claim 1 is administered to a patient in a therapeutically effective amount.

22. The chemically modified glycosaminoglycan according to claim 1, wherein the non-reducing end unsaturated glucosamines are present as signals in the interval of 5.0 to 6.5 ppm in a $^1$H-NMR spectrum with an intensity (% ratio) of less than 4% in relation to the signal at 5.42 ppm from native heparin.

23. The chemically modified glycosaminoglycan according to claim 16, wherein the non-reducing end unsaturated glucosamines are present as signals in the interval of 5.0 to 6.5 ppm in a $^1$H-NMR spectrum with an intensity (% ratio) of less than 4% in relation to the signal at 5.42 ppm from native heparin.

24. The chemically modified glycosaminoglycan according to claim 22, wherein the modified glucosamines produce signals at 5.95 ppm and 6.15 ppm in an $^1$H-NMR spectrum.

* * * * *

UNITED STATES PATENT AND TRADEMARK OFFICE
CERTIFICATE OF CORRECTION

Page 1 of 2

PATENT NO.        : 9,475,888 B2
APPLICATION NO.   : 14/366624
DATED             : October 25, 2016
INVENTOR(S)       : Ekre et al.

It is certified that error appears in the above-identified patent and that said Letters Patent is hereby corrected as shown below:

In the Drawings

Replace the image of the sole figure with the following image attached.

In the Claims

Claim 1, at Column 24, Line 49, replace "mass" with --weight--.

Signed and Sealed this
Fifth Day of June, 2018

Andrei Iancu
*Director of the United States Patent and Trademark Office*